United States Patent [19]

Stabell

[11] 3,999,867
[45] Dec. 28, 1976

[54] SAMPLING CELL OF SALT CRYSTALS AMALGAMATED TO METAL SPACER

[75] Inventor: William S. Stabell, Norwalk, Conn.

[73] Assignee: Wilks Scientific Corporation, South Norwalk, Conn.

[22] Filed: Apr. 2, 1975

[21] Appl. No.: 564,497

[52] U.S. Cl. .............................. 356/246; 156/107; 250/576; 356/181
[51] Int. Cl.² ........................................ G01N 1/10
[58] Field of Search ........... 356/181, 246; 250/576; 156/107; 65/59 R, 154

[56] References Cited
UNITED STATES PATENTS

| 3,391,447 | 7/1968 | Ard .................................. 356/246 |
| 3,552,865 | 1/1971 | Leung et al. ...................... 356/246 |
| 3,751,173 | 8/1973 | Sanz et al. ........................ 356/246 |

Primary Examiner—Vincent P. McGraw
Attorney, Agent, or Firm—Buckles and Bramblett

[57] ABSTRACT

An improvement in the method of assembling a pair of windows and a spacer by amalgamation to form a sampling cell. The improvement comprises evaporatively depositing a thin layer of metal on each of the windows prior to amalgamating them with the spacer.

8 Claims, 3 Drawing Figures

3,999,867

SAMPLING CELL OF SALT CRYSTALS AMALGAMATED TO METAL SPACER

BACKGROUND OF THE INVENTION

This invention pertains to the manufacture of liquid sampling cells of the type utilized in spectrophotometers. Such cells normally comprise a pair of windows transparent to the radiation to be employed, bonded to and separated by a metallic spacer which defines the sample space. For spectrophotometry in the infrared region, these windows are customarily made of salt crystals. Commonly used salts for this purpose are sodium chloride, potassium bromide, calcium fluoride, barium fluoride, thallium bromide iodide, cesium iodide, cesium bromide, silver chloride, and zinc selenide. Spacers are usually copper or lead and may vary from 0.015 to 1.0 mm in thickness.

The usual method of assembling a sample cell includes the steps of cleaning the crystal windows and the spacer. The spacer is then dipped in mercury and sandwiched between the windows. It is then allowed to sit under pressure two or three days.

The difficulty with the prior art procedure set forth above, is that the bond between the spacer and the crystals is not always adequate. In fact, the failure rate in producing cells by this technique is approximately 50%. Furthermore, the bond, even when technically adequate, often has a splotchy appearance.

For the foregoing reasons, it is a primary object of this invention to provide an improved method of manufacturing sealed cells for use in spectrophotometers. Other objects are: to provide such a method wherein improved sealing is obtained between the crystal windows and the spacer; wherein the failure rate in manufacture of the cells is substantially reduced; and wherein the appearance of the cells is improved. The manner in which the foregoing objects are achieved will be best understood by reference to the following description and appended claims.

SUMMARY OF THE INVENTION

An improvement in the method of making a radiation absorption sampling cell including (a) providing a first window transparent to the radiation of interest and having at least one plane surface, the window defining spaced fluid flow channels communicating with its plane surface, (b) providing a second window which is also transparent to the radiation of interest and has at least one plane surface, and (c) providing an annular metallic spacer having opposed plane surfaces. The improvement comprises depositing on each of the plane surfaces of each of the windows a metallic film. The film surrounds and defines an uncoated sample region on each of the surfaces. The sample region on the first window includes the fluid flow channels. The first and second plane surfaces of the spacer are coated with mercury and the spacer is mounted between the metallic coated plane surfaces of the first and second windows to form amalgams with the spacer and the films.

DESCRIPTION OF THE PREFERRED EMBODIMENT

Figure 1:
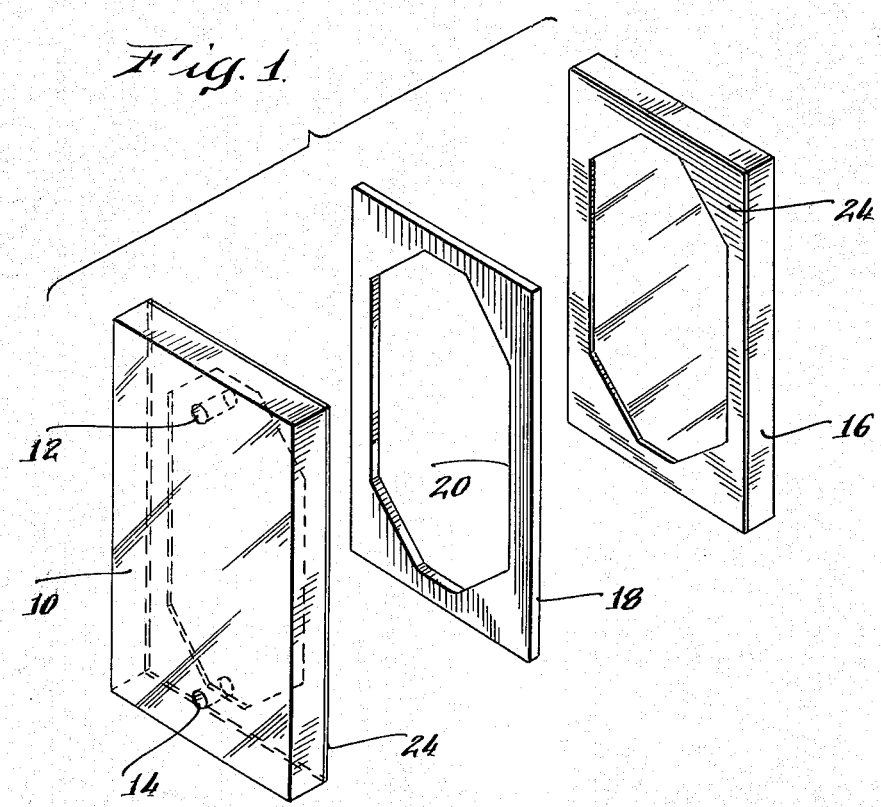
FIG. 1 is an exploded view of a cell constructed in accordance with this invention.

With particular reference to FIG. 1, there are illustrated in exploded form the components of a sampling cell constructed in accordance with the present invention. These components include a crystal window 10 defining inlet 12 and outlet 14 passages therethrough, a second crystal window 16, and a metal spacer 18 defining a central sample space 20. Both windows and the spacer are substantially rectangular, of the same size, and have their major surfaces planar. The size of the opening 20 is such that, when sandwiched together in alignment, the passages 12, 14 communicate with the interior of the sample space 20.

Figure 2:
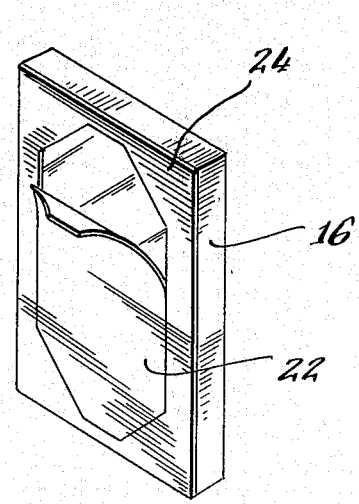
FIG. 2 is an illustration of one of the windows illustrating one step in the practice of the invention.

After preparation of the windows, a mask 22 in the shape of sample space 20 is applied to one of the major surfaces of each window. A thin film 24 of metal is then evaporatively deposited on each masked surface by techniques well known in the art and the mask 22 thereafter removed as shown in FIG. 2. In the drawings, the thickness of the metal film layer is greatly exaggerated for purposes of illustration. Various film materials and thickness may be employed. However, in one example each window is first coated with nichrome to a thickness of 500 A and thereafter gold is deposited over the nichrome to a thickness of 1,000 A. Other materials such as, for example, copper or lead, could be utilized in place of gold.

Figure 3:
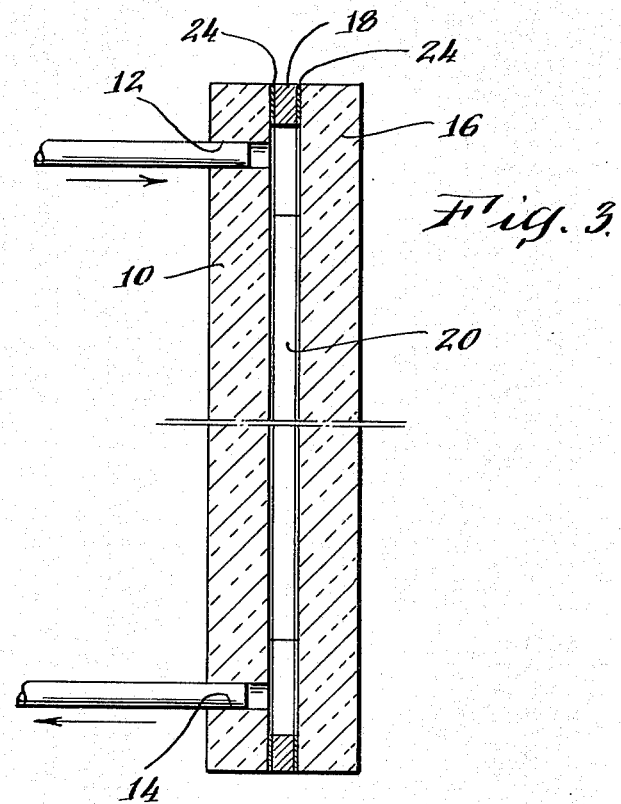
FIG. 3 is an enlarged vertical cross-section taken through a cell constructed in accordance with the invention.

The spacer is cleaned and etched and then dipped in mercury. In the case of copper spacers, they are sequentially dipped in salt water solution, distilled water, and acetic acid prior to being dipped in mercury. Lead spacers are dipped in stannous chloride prior to dipping in mercury. After the mercury dip, excess mercury is wiped from the spacer and it is thereafter sandwiched between the coated windows 10, 16, as shown in FIG. 3. The assembly is mounted in a suitable holder under pressure and held for 2 to 3 days. The mercury coating on the spacer 18 amalgamates with the spacer material and also with the metallic films 24 of both windows, forming therewith a tight, uniform, and leak-proof seal.

It will be appreciated by those skilled in the art that a number of variations and modifications may be made in this invention without departing from its spirit and scope. Accordingly, the foregoing description is to be taken as illustrative only, rather than limiting. This invention is limited only by the scope of the following claims.

I claim:

1. In the method of making a radiation absorption sampling cell including (a) providing a first window transparent to the radiation of interest and having at least one plane surface, said first window defining spaced first and second fluid flow channels communicating with said plane surface, (b) providing a second window transparent to the radiation of interest and having at least one plane surface, and (c) providing an annular metallic spacer having opposed first and second plane surfaces, the improvement which comprises: depositing on said plane surfaces of each of said windows a metallic film, said film surrounding and defining an uncoated sample region on each of said surfaces, the sample region of said first window including said fluid flow channels; coating the first and second plane surfaces of said spacer with mercury; and mounting said spacer between the metallic coated plane surfaces of said first and second windows to form amalgams with said spacer and said films.

2. The improvement of claim 1 wherein said metallic film is evaporatively deposited on said windows.

3. The improvement of claim 2 wherein said film depositing step includes applying a mask to each of said windows prior to depositing said film and thereafter removing said mask.

4. The improvement of claim 1 wherein said film depositing step comprises: evaporating a first metal film on the window surface; and evaporating a second metal film on the first film.

5. A radiation absorption sampling cell which comprises: first and second radiation transparent windows, each having at least one plane surface; a thin metallic layer deposited on each of said plane surfaces; and a metallic spacer having opposed plane surfaces amalgamated to the respective metallic layers and defining a sample space between said windows.

6. The improvement of claim 5 wherein said windows are salt crystals.

7. The improvement of claim 6 wherein said windows are selected from the group consisting of sodium chloride, potassium bromide, calcium fluoride, barium fluoride, thallium bromide iodide, cesium iodide, cesium bromide, silver chloride, and zinc selenide.

8. The cell of claim 5 wherein each of said metallic layers comprises a layer of gold deposited on a dissimilar metal substrate.

* * * * *